United States Patent

Bukowsky

[11] Patent Number: 6,093,374
[45] Date of Patent: Jul. 25, 2000

[54] POTPOURRI STIRRER AND REFRESHER DEVICE

[76] Inventor: Clifton R. Bukowsky, 3844 Shore Crest, Dallas, Tex. 75209

[21] Appl. No.: 09/178,673

[22] Filed: Oct. 26, 1998

[51] Int. Cl.[7] ........................................ A61L 9/04
[52] U.S. Cl. .................... 422/306; 422/123; 422/124; 422/305; D23/366; 261/DIG. 17; 261/DIG. 65; 366/325.94; 366/349
[58] Field of Search .................. 422/4, 5, 120, 422/123–126, 293, 305, 306; D07/373; D23/366; 392/386; 261/DIG. 17, DIG. 65

[56] References Cited

U.S. PATENT DOCUMENTS

| Re. 34,847 | 2/1995 | Muderlak et al. | 222/25 |
| 3,872,604 | 3/1975 | Keller | 34/9 |
| 4,601,886 | 7/1986 | Hudgins | 422/305 |
| 5,498,397 | 3/1996 | Horng | 422/124 |
| 5,908,140 | 6/1999 | Muderlak et al. | 222/1 |

Primary Examiner—Terrence R. Till
Assistant Examiner—Fariborz Moazzam
Attorney, Agent, or Firm—David H. Judson

[57] ABSTRACT

An automated device for periodically revitalizing potpourri can be placed in a potpourri container. The device includes a mixing element for mixing potpourri and an aerosol canister containing a fragrance oil for adding fragrance to the potpourri. A battery powered motor periodically rotates the mixing element to stir the potpourri and activates the aerosol canister to dispense the fragrance oil into the potpourri. The device thus uniformly mixes the fragrance into the potpourri. Electric timer circuitry is provided to activate the device on a preset periodic basis.

16 Claims, 3 Drawing Sheets

POTPOURRI STIRRER AND REFRESHER DEVICE

BACKGROUND OF THE INVENTION

1. Technical Field

The present invention relates generally to potpourri and, more particularly, to a time-activated potpourri stirring and refreshing device.

2. Description of the Related Art

Many households use potpourri, which is typically a combination of dried flower petals, spices and other substances, to provide decor and fragrance to various rooms. However, the fragrance of potpourri generally lasts only a short time, requiring constant potpourri replacement.

The amount of fragrance released by potpourri is generally related to the surface area of the potpourri petals exposed to the environment. Thus, periodically mixing potpourri allows different petals to be exposed and extends the time fragrance is released. Potpourri replacement at some point is nevertheless needed.

An alternative to replacing potpourri is to revitalize or refresh the scent by periodically adding fragrance oil to the potpourri and mixing it. This, however, is a tedious and repetitive process.

Thus, there is a need for a device for automatically refreshing potpourri.

BRIEF SUMMARY OF THE INVENTION

A primary object of this invention is to provide an automated device for mixing and refreshing potpourri.

A further object of this invention is to provide an automated device for mixing fragrance oil in potpourri.

Another object of this invention is to provide an automated device that is sized and configured to fit within ordinary potpourri containers for mixing and refreshing potpourri.

Yet another object of the invention is to provide a device for mixing and refreshing potpourri on a preset time-activated basis.

Still another object of this invention is to provide an automated device for mixing and refreshing potpourri having a mixer with adjustable paddles.

These and other objects are accomplished by an automated device placeable in a potpourri container for periodically revitalizing potpourri. The device includes a mixing element for mixing potpourri and a sprayer (such as an aerosol canister) containing a fragrance oil for adding fragrance to the potpourri. A battery powered motor rotates the mixing element to stir the potpourri and activates the sprayer to spray the fragrance oil into the potpourri. The device thus uniformly mixes the fragrance oil into the potpourri. Electric timer circuitry is provided to activate the device on a preset periodic basis.

The foregoing has outlined some of the more pertinent objects and features of the present invention. These objects should be construed to be merely illustrative of some of the more prominent features and applications of the invention. Many other beneficial results can be attained by applying the disclosed invention in a different manner or modifying the invention as will be described. Accordingly, other objects and fuller understanding of the invention may be had by referring to the following Detailed Description of the Preferred Embodiment.

BRIEF DESCRIPTION OF THE DRAWINGS

For a more complete understanding of the present invention and the advantages thereof, reference should be made to the following detailed description taken in connection with the accompanying drawings in which.

DETAILED DESCRIPTION OF THE PREFERRED EMBODIMENT

Figure 1:
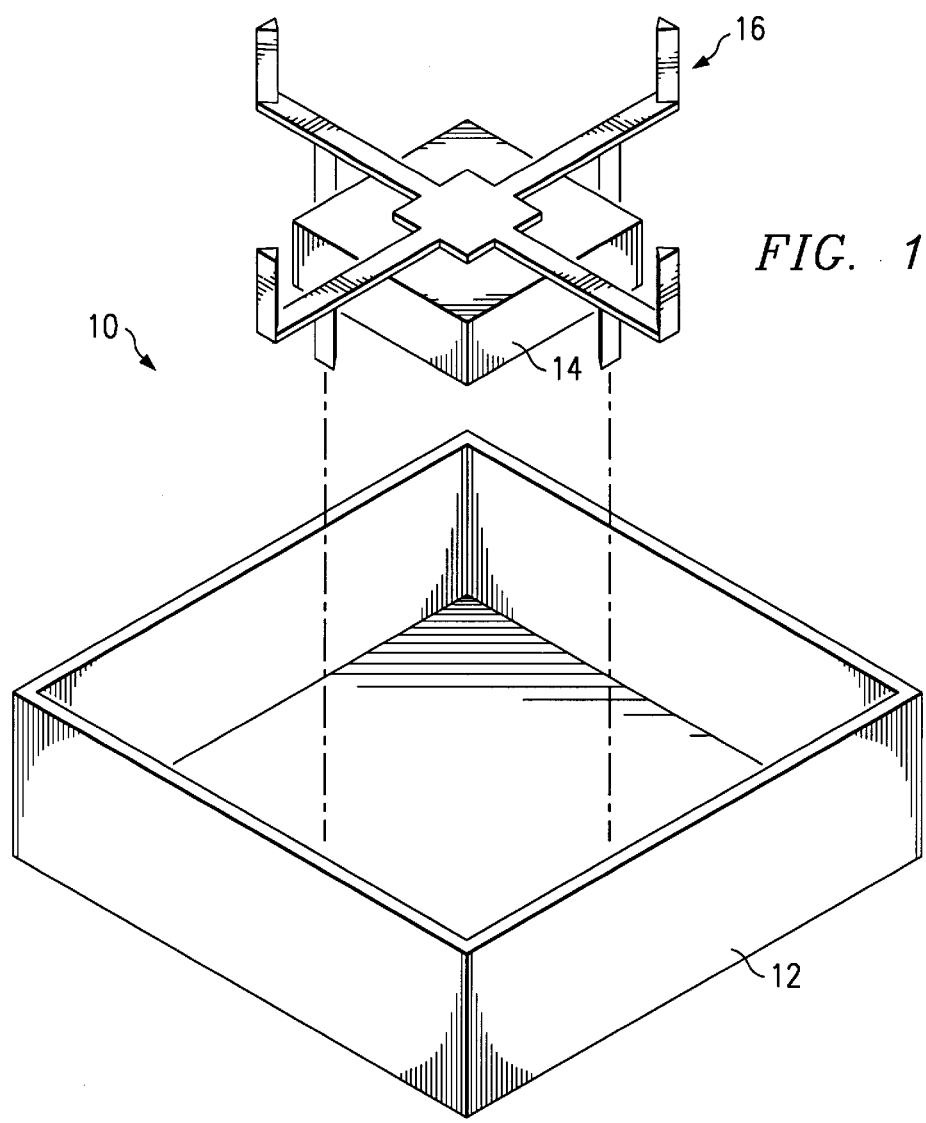
FIG. 1 is a perspective view of the inventive potpourri stirrer and refresher device along with an ordinary potpourri container.

FIG. 1 illustrates a potpourri stirrer and refresher device 10 in accordance with the present invention. The stirrer device 10 is placed inside an ordinary potpourri container or bowl 12, which is then filled with potpourri (not shown) to be periodically revitalized by the device 10. Although not required, the device 10 can be attached to the bowl by various means including, e.g., a VELCRO hook-and-loop fastener (not shown).

Figure 2:
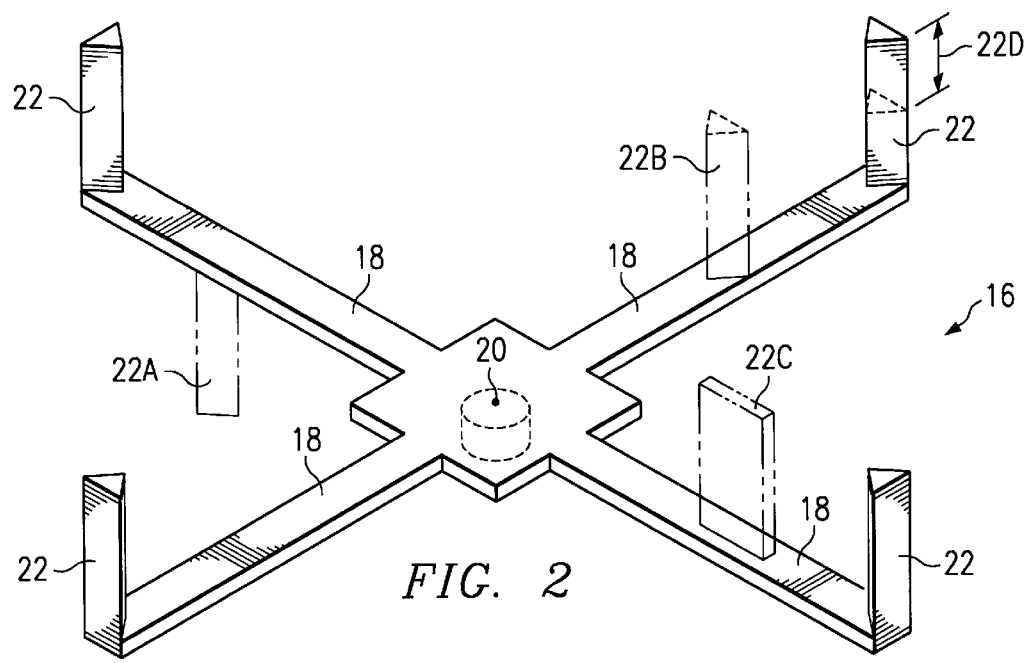
FIG. 2 is an enlarged perspective view of the mixing element of the inventive potpourri stirrer and refresher device.

The stirrer and refresher device 10 comprises a base 1 4 and a mixing element 16 (shown in the form of a paddle set). As shown in FIG. 2, the mixing element 16 preferably includes four arms 1 8 extending radially from a center point 20. A paddle 22 extends upwardly from the distal end of each arm 18. As will be described below, as the mixing element 16 rotates about the center point 22, the paddles 22 move through and mix potpourri in the container 12.

The particular arrangement, shape and size of the paddles 22 can be varied as desired. For example, as shown in FIG. 2, the paddles 22A, 22B can be provided to extend from the underside of the arms and at locations somewhere along the lengths of the arms 18. In addition, the paddles can be of varying shapes as indicated by paddle 22C. Also, the paddles may include break-away portions 22D that allow their heights to be adjusted by a user. A user can select a mixing element having a particular size and paddle arrangement to fit a given sized container 12.

The mixing element 16 can comprise a variety of materials. It is preferably extruded or injection molded plastic.

Figure 3:
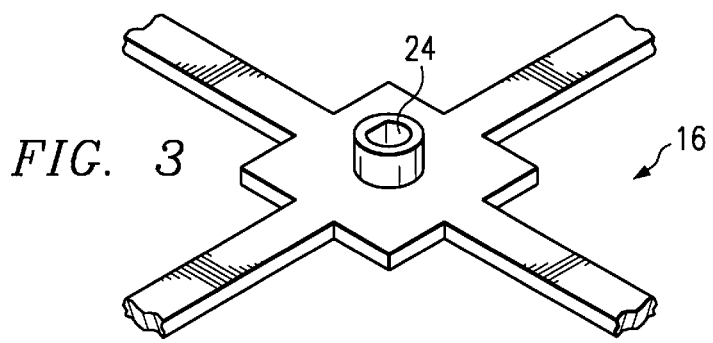
FIG. 3 is a perspective view of a portion of the underside of the mixing element.

The underside of the mixing element 16 shown partially in FIG. 3 includes a shaft hole 24 at the center point 20 for receiving a motor shaft, which will be described further below. As the motor shaft turns, the paddles in the mixing element mix potpourri in the container 12.

Figure 4:
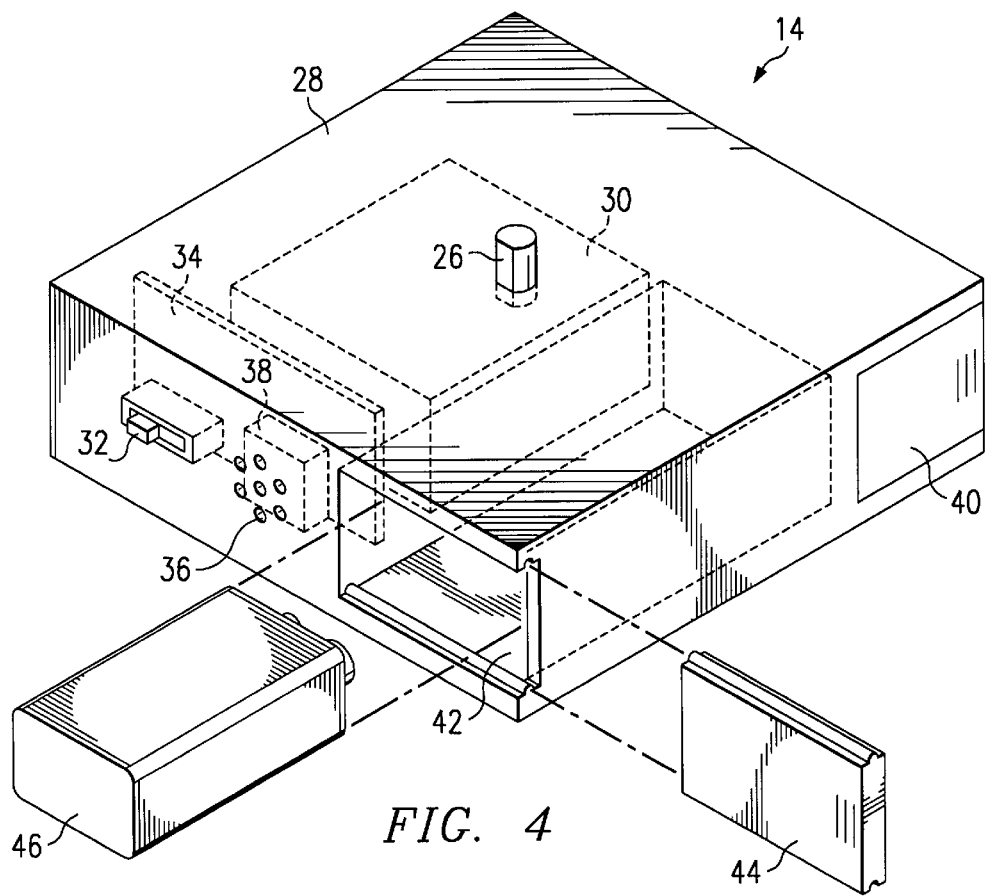
FIG. 4 is a is a perspective view of the base of the inventive device.

FIG. 4 shows the stirrer base 14 in greater detail. A keyed motor shaft 26, which fits in the hole 24 of the mixing element 16 and rotates it, extends from the base housing 28. The motor shaft 26 is driven by a motor 30 within the housing 28. The base 14 has an on/off switch 32 connected to a timer control circuit board 34 containing circuitry for periodically activating the device 10. The housing 28 also includes openings 36 for an optional audible alarm 38. There is a cover 40 for a fragrance canister compartment 41 (shown in FIG. 5). In addition, the housing 28 includes a battery compartment 42 with a compartment cover 44 for a battery 46, e.g., a nine volt battery for powering the device 10.

Figure 5:
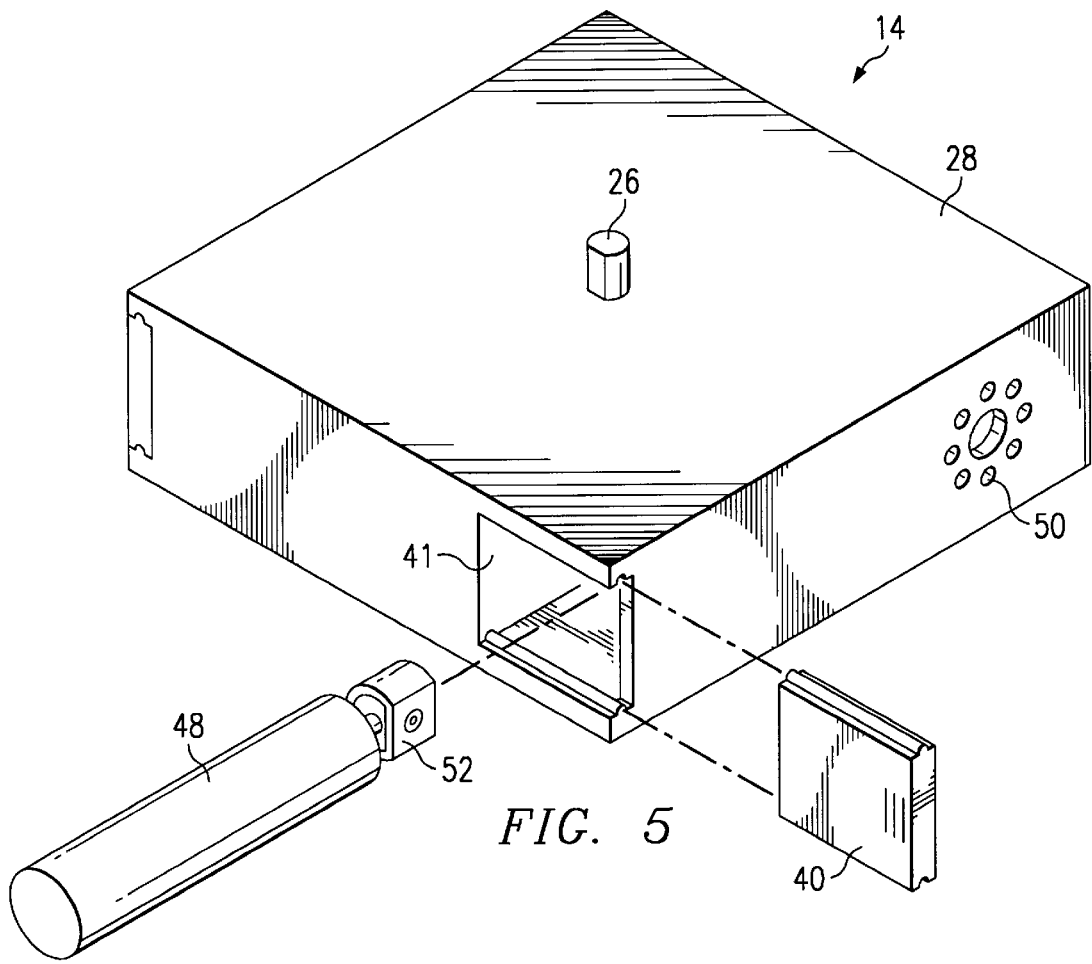
FIG. 5 is a is a further perspective view of the base.

As shown in FIG. 5, a sprayer, preferably an aerosol canister 48, which contains a fragrance oil product, is placed in the aerosol compartment 41. The base housing 28 includes openings 50 for allowing the fragrance oil from the canister 48 to dispensed for refreshing the potpourri. The aerosol canister 48 includes a cap 52, which is preferably keyed to assure that it is properly placed in the compartment 42 such that spray from the canister 48 is directed out of the openings 50.

Figure 6:
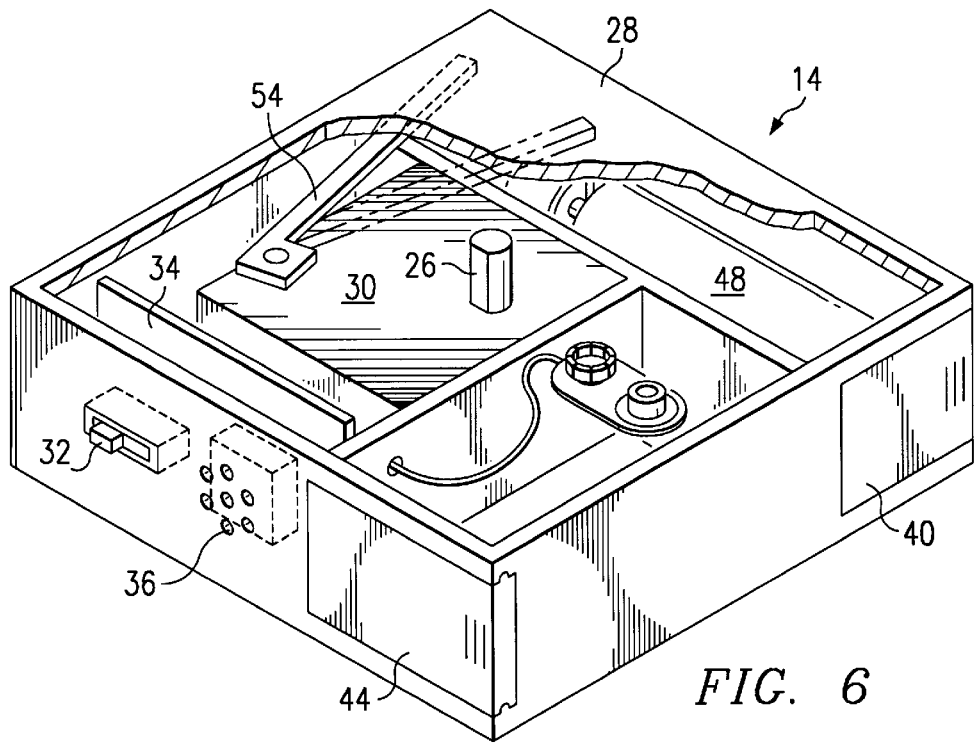
FIG. 6 is a is a perspective view of the base with the outer housing thereof shown partly removed to illustrate the base interior.

FIG. 6 shows the electric motor 30, which powers the motor shaft 26. Additionally, the electric motor 30 powers an aerosol activation armature 54, which extends into the aerosol canister compartment and engages the aerosol canister 48 as will be described below. The electrical timer circuitry board 34 allows for remote or time activation of the motor.

The aerosol canister 48 contains a scented substance such a fragrance oil for refreshing the potpourri scent. While in the stirring mode, the motor 30 drives the activation armature 54 into engagement with the cap 52 of the aerosol canister 48. This action depresses the cap 52 and prompts the aerosol canister 48 to dispense the fragrance oil through the openings 50 in the base 14 and into the potpourri mix. The oil is preferably dispensed as a spray so as not to overly soak any particular potpourri piece. Such soaked pieces have the tendency to migrate to the bottom of the container 12 and not provide much useful fragrance benefit.

In the preferred embodiment, the circuitry board 34 allows the user to determine a time interval for the stirrer device 10 to be activated. The optional audible alarm within the base 14 is responsive to a signal from the circuit board 34 to provide a warning that the stirrer device 10 is being activated.

In an alternative embodiment of the invention, the potpourri stirrer and refresher device comprises a built-in attachment to a potpourri container.

It should be appreciated by those skilled in the art that the specific embodiments disclosed above may be readily utilized as a basis for modifying or designing other devices for carrying out the same purposes of the present invention. It should also be realized by those skilled in the art that such equivalent constructions do not depart from the spirit and scope of the invention as set forth in the appended claims.

Having thus described my invention, what I claim as new and desire to secure by Letters Patent is set forth in the following claims:

1. A device for revitalizing potpourri in a potpourri container, comprising:
   a motor within the container, the motor having a fixed position relative to the container;
   a mixing element within the container and attached to the motor for mixing potpourri, the mixing element being moved relative to the container by the motor;
   a fragrance supply for adding a scented substance to the potpourri, the fragrance supply being within the container and having a fixed position relative to the motor; and
   means for dispensing the scented substance from the fragrance supply.

2. The device of claim 1, wherein said mixing element comprises at least one arm having a paddle attached thereto.

3. The device of claim 1 wherein said mixing element comprises a plurality of arms extending radially from a center point with each arm having a paddle attached thereto.

4. The device of claim 1 wherein the fragrance supply comprises an aerosol canister containing fragrance oil.

5. The device of claim 1 wherein the means for dispensing comprises an armature extending from the motor for causing the scented substance from the fragrance supply to be released.

6. The device of claim 1 further comprising means for periodically activating the motor.

7. The device of claim 6 further comprising means for sounding an alarm when the motor is activated.

8. The device of claim 1 wherein said device is battery-powered.

9. A potpourri refreshing apparatus, comprising:
   a bowl for holding potpourri; and
   a device in said bowl for stirring and refreshing the potpourri, said device comprising:
   a mixing element for mixing the potpourri;
   a fragrance supply for adding a scented substance to the potpourri; and
   means for moving the mixing element and for dispensing the scented substance from the fragrance supply.

10. The potpourri refreshing apparatus of claim 9, wherein said mixing element comprises at least one arm having a paddle attached thereto.

11. The potpourri refreshing apparatus of claim 9 wherein said mixing element comprises a plurality of arms extending radially from a center point with each arm having a paddle attached thereto.

12. The potpourri refreshing apparatus of claim 9 wherein the fragrance supply comprises an aerosol canister containing fragrance oil.

13. The potpourri refreshing apparatus of claim 9 wherein the means for moving and dispensing comprise a motor having a rotatable motor shaft attached to the mixing element and an armature for causing the scented substance from the fragrance supply to be released.

14. The potpourri refreshing apparatus of claim 9 wherein said device further comprises means for periodically activating said means for moving and dispensing.

15. The potpourri refreshing apparatus of claim 14 wherein the device further comprises means for sounding an alarm when said means for moving and dispensing are activated.

16. The potpourri refreshing apparatus of claim 9 wherein said device is battery-powered.

* * * * *